US00PP22802P2

(12) United States Plant Patent
Yates

(10) Patent No.: US PP22,802 P2
(45) Date of Patent: Jun. 19, 2012

(54) *BEGONIA* PLANT NAMED 'YABON'

(50) Latin Name: *Begonia boliviensis*
Varietal Denomination: YABON

(76) Inventor: Frederic C. Yates, Congleton (GB)

( * ) Notice: Subject to any disclaimer, the term of this patent is extended or adjusted under 35 U.S.C. 154(b) by 299 days.

(21) Appl. No.: 12/799,003

(22) Filed: Apr. 15, 2010

(51) Int. Cl.
*A01H 5/00* (2006.01)

(52) U.S. Cl. ..... Plt./343

(58) Field of Classification Search ..... Plt./343
See application file for complete search history.

(56) References Cited

U.S. PATENT DOCUMENTS

PP19,777 P2 * 2/2009 Yates ..... Plt./343
PP19,817 P2 * 3/2009 Yates ..... Plt./343
PP20,093 P3 * 6/2009 Yates ..... Plt./343

OTHER PUBLICATIONS

UPOV ROM GTITM Computer Database, GTI Jouve Retrieval Software 2011/10 Citation for 'YABON'.*
Anonymous. "Bon Bon Sherbert Begonia" Available at http://www.Ballhort.com Accessed Sep. 30, 2011.*

* cited by examiner

*Primary Examiner* — Wendy C Haas
(74) *Attorney, Agent, or Firm* — Penny J. Aguirre

(57) ABSTRACT

A new cultivar of *Begonia boliviensis* named 'YABON', characterized by its large semi-double flowers that are yellow in color, its spreading and upright habit, its abundant production of floriferous side shoots, and its vigorous growth habit.

2 Drawing Sheets

Botanical classification: *Begonia boliviensis.*
Cultivar designation: 'YABON'.

RELATED APPLICATIONS

This application is co-pending with U.S. Plant Patent applications filed for cultivars derived from the same breeding program entitled *Begonia* Plant Named 'YAMOUR' (U.S. Plant patent application Ser. No. 12/798,976), *Begonia* Plant Named 'YAGANCE' (U.S. Plant Pat. No. 19,817), *Begonia* Plant Named 'YAMANCE' (U.S. Plant Pat. No. 19,777), and *Begonia* Plant Named 'YABOS' (U.S. Plant Pat. No. 20,093).

BACKGROUND OF THE INVENTION

The present invention relates to a new and distinct cultivar of *Begonia* plant, botanically known as *Begonia boliviensis* 'YABON' and will be referred to hereafter by its cultivar name, 'YABON'.

The new cultivar was derived from a controlled breeding program conducted by the Inventor at his nursery in Congleton, Cheshire, U.K. The overall purpose of the breeding program established in 2003 is to make selections of *Begonia* plants with compact plant habits suitable for container use combined with superior flower performance and productive stock plants for propagation. 'YABON' was selected in the Inventor's greenhouse in 2006 as a single unique plant from amongst the seedlings derived from a cross made in 2005 between two unnamed, proprietary plants of *Begonia boliviensis* as the parents.

Asexual reproduction of the new cultivar was first accomplished by terminal stem cuttings in Congleton, Cheshire, U.K. in 2007 by the Inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'YABON' as a new and distinct cultivar of *Begonia.*

1. 'YABON' exhibits large, semi-double yellow flowers.
2. 'YABON' exhibits a spreading and upright habit.
3. 'YABON' readily produces floriferous side shoots.
4. 'YABON' exhibits a vigorous growth habit.

The parent plants of 'YABON' both differ from 'YABON' in having smaller leaves and more upright plant habits. 'YABON' can be compared to 'YABOS'. 'YABOS' differs from 'YABON' in having a more pendulous plant habit, a less vigorous growth habit and in having single red-orange flowers. 'YABON' can also be compared to other cultivars from the same breeding program. 'YAMOUR' differs from 'YABON' in having a semi-pendulous habit, darker leaves, and red flowers. 'YAGANCE' differs from 'YABON' in having bicolor pink and white flowers and 'YAMANCE' differs from 'YABON' in having flowers that are pink in color.

BRIEF DESCRIPTION OF THE DRAWING

The accompanying colored photographs illustrate the overall appearance and distinct characteristics of the new *Begonia.*

The photographs were taken in Congleton, Cheshire, U.K. of a 3-liter container planted with 4 plant of 'YABON' grown in 4½ inch pots, the plants are about 6 months in age.

Figure 1:
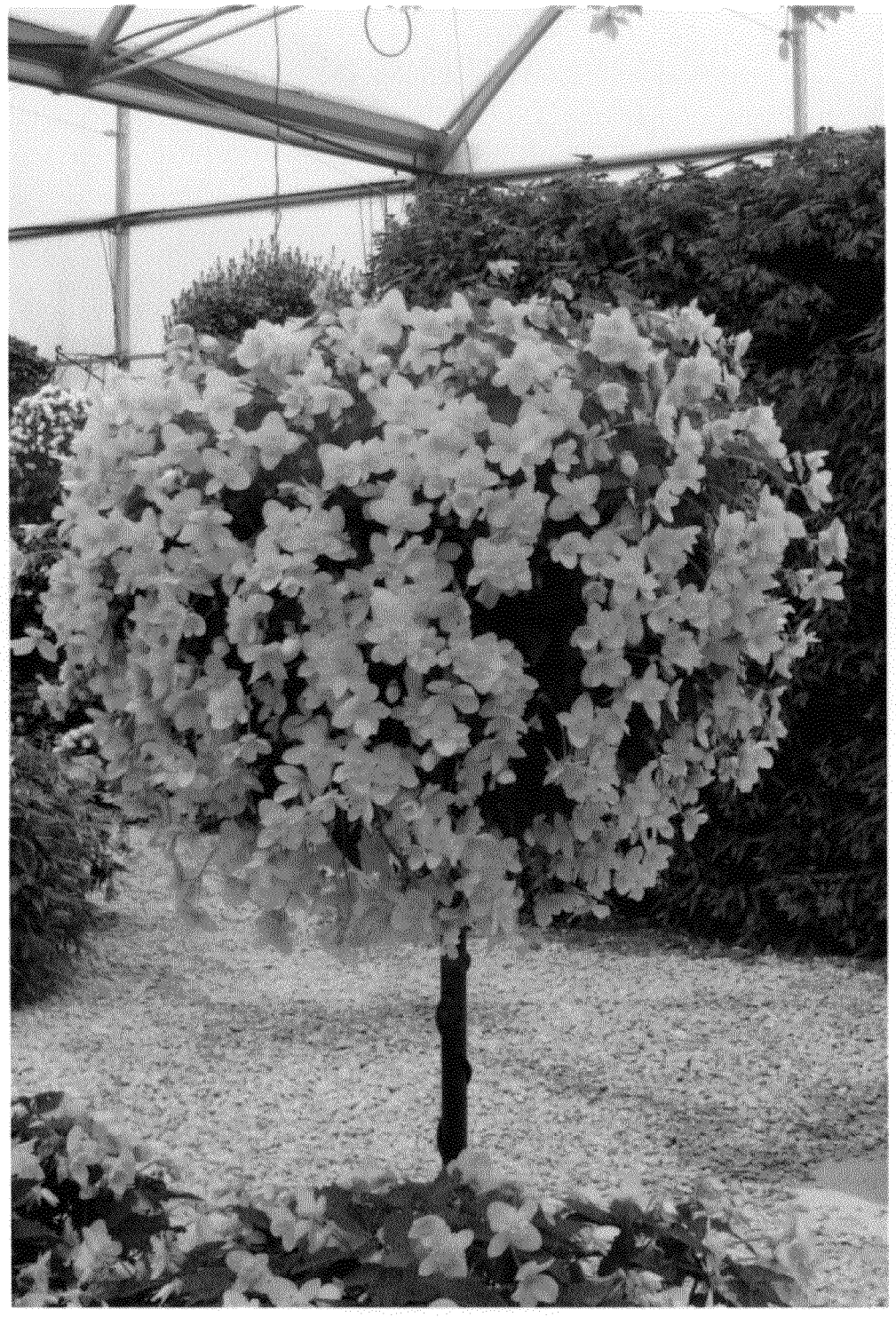

The photograph in FIG. 1 provides a view of the habit and floriferous nature of 'YABON'.

Figure 2:
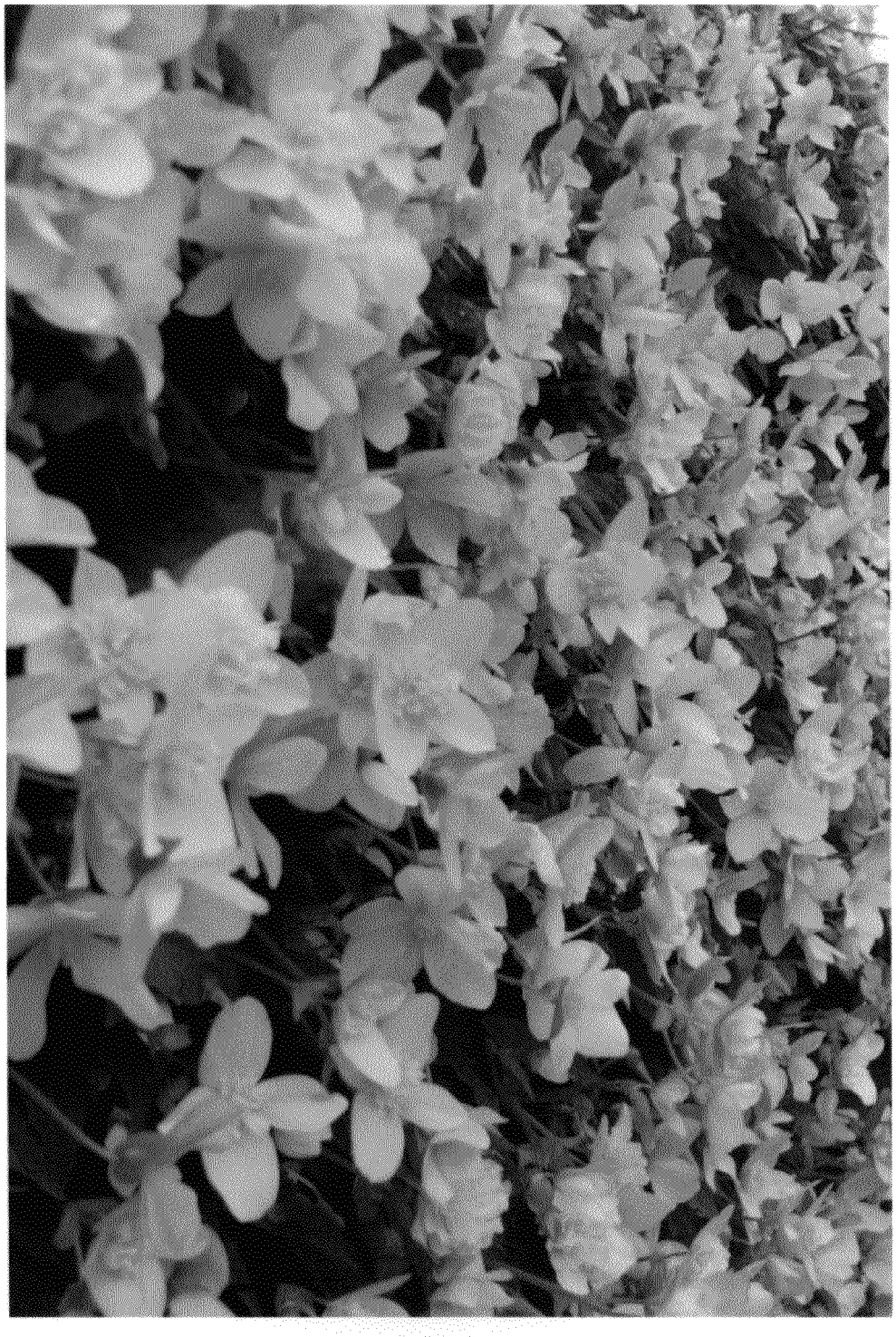

The photograph in FIG. 2 provides a close-up view of the flowers of 'YABON'.

The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately 4 months in age as grown in 4½ inch containers under greenhouse conditions with ambient light in Liss, Hampshire, U.K. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General plant characteristics:

*Plant type*.—Deciduous tuberous perennial, grown primarily for use in baskets, and containers.

*Plant habit*.—Spreading and upright, freely-branching.

*Flowering period*.—From May to October.

*Height and spread*.—Reaches about 30 cm in height and spread.

*Cold hardiness*.—U.S.D.A. Zone 10.

*Culture*.—Grows in any commercial soil or growing media, 12 hours of light is needed and 20° C. for production in the winter months.

*Diseases and pests*.—No susceptibility or resistance to diseases or pests has been observed.

*Root description*.—Fleshy to fibrous with tubers produced for over-wintering.

*Tubers*.—Slightly flattened, irregularly lobed, slightly depressed in centre, an average of 4 cm in length, 3 cm in height and 2.5 cm in width (larger in older plants), surface is smooth and slightly corky, 166C in color with corky patches 177B in color.

Growth and propagation:

*Growth rate*.—Vigorous.

*Propagation*.—Terminal stem cuttings.

*Time required for root initiation*.—10 to 14 days at 20° C.

*Time required for root development*.—5 to 8 weeks to reach commercial size.

Stem description:

*Stem size*.—Average of 13.0 cm in length and 5 mm in width with lateral branches about 3 mm in width.

*Stem shape*.—Round, solid.

*Stem color*.—173D and flushed with 179B in full sun.

*Stem surface*.—Pubescent with simple hairs, lenticels absent.

*Internode length*.—Average of 2.7 cm.

*Branching habit*.—Freely branched.

*Branching angle at emergence*.—About 45°.

Foliage description:

*Leaf shape*.—Lanceolate, strongly asymmetric with one side narrowly ovate, the other narrowly cordate and wider.

*Leaf division*.—Entire.

*Leaf base*.—Cordate.

*Leaf apex*.—Acuminate.

*Leaf venation*.—Pinnate, color 146D on upper surface and 145C on lower surface.

*Leaf margins*.—Serrate with short bristles emerging from tips of the teeth.

*Leaf attachment*.—Petiolate.

*Leaf arrangement*.—Alternate.

*Leaf surface*.—Upper surface; occasional short colorless hairs, lower surface; pubescent with short simple colorless hairs.

*Leaf color*.—Upper surface; 146B to 146C, lower surface; 145B and tinged with 184D on inter-venal regions on older leaves.

*Leaf size*.—Average of 7.2 cm in length and 3.4 cm in width.

*Leaf quantity*.—Average of 14 per branch.

*Leaf fragrance*.—None.

*Petioles*.—Average 1.8 cm in length and 2 mm in width, pubescent with simple hairs, color is 151D and faintly flushed with 170C.

*Stipules*.—Broadly triangular in shape, becoming dry and papery, about 3 mm in length and 4 mm in width, 195D in color.

Flower description:

*Inflorescence type*.—2 to 3 flowered cyme produced sequentially in the axils of the upper leaves, monoecious with terminal male flowers developing before the 2 lateral female flowers, male flowers are semi-double due to petaloid stamens.

*Peduncles*.—About 5.5 cm in length and 2.0 mm in width, color; 145A flushed with 181B on exposed side, occasionally pubescent with simple colorless hairs.

*Flower persistence*.—Self-cleaning.

*Flower type*.—Female single, male double.

*Flower fragrance*.—None.

*Flower number*.—Average of 10 per inflorescence, one inflorescence per stem.

*Flower aspect*.—Hanging.

*Bracts*.—2, present at base of cyme, primarily round in shape, occasional bristles on margin, about 11 mm in length and width, color is 195B and strongly flushed with 181C at margins.

Male flowers:

*Pedicels*.—About 1.9 cm in length and 1.5 mm in width, 47B in color on exposed side, 29C in color on shaded side, glabrous surface.

*Flower buds*.—Flattened rotund in shape, about 1.6 cm in length and 1.5 cm in width, color is 2B and flushed with 37C on exposed side.

*Flower size*.—About 1.8 cm in length and ranging from 4.9 cm to 6.2 cm in width, average 5.8 cm in width.

*Tepals*.—4 in number (2 inner and 2 outer), outer tepals; broadly ovate in shape, obtuse apex, broadly cuneate base, average of 2.8 cm in length and 2.1 cm in width, glabrous and smooth surface, entire margin, color of inner and outer surface 11D and fading to 11C at the base with outer surface faintly flushed with 49B.

*Corolla form*.—Flared, tepals are un-fused.

*Stamens*.—Petaloid, numerous, elliptic in shape, inner ones slightly twisted, cuneate at base, outer stamens 2.1 mm in length and 9.0 mm in width, inner stamens 1.7 mm in length and 7.0 mm in width, 11B in color, outer and inner surface 11C becoming 11B in center and 11A at extreme base.

*Filaments*.—Absent.

*Anthers*.—Absent.

*Pollen*.—Absent.

Female flowers:

*Pedicels*.—Average 2.9 cm in length and 1.5 mm in width, color; 47B on exposed side, 29C on shaded side, glabrous surface.

*Flower buds*.—Flattened ovoid in shape, about 1.6 cm in length and 1.2 cm in width, 2D in color to 37C on exposed side.

*Flower size*.—About 1.1 cm in length (excluding ovary) and 5.2 cm in width.

*Tepals*.—5 in number (3 inner and 2 outer), outer tepals; ovate in shape, acute to obtuse apex, rounded base, average of 2.9 cm in length and 2.0 cm in width, glabrous and smooth surface, entire margin, 11D in color shading to 11C at the base and faintly flushed with 49B, inner tepals; narrowly ob-ovate in shape, obtuse apex, narrowly cuneate base, average of 2.9 cm in length and 1.6 cm in width, glabrous and smooth surface, entire margin, slightly darker than 11D and 11C at base.

*Corolla form*.—Flared, tepals are un-fused.

*Styles*.—3 in number, cylindrical, connate at base for <1 mm, about 3 mm in length and <1 mm in width, 12B in color.

*Stigmas*.—Bifid in shape, stigmatic surfaces twisted around extensions of the style, lobes about 3 mm in length and <1 mm in width, 12A in color.

*Ovaries*.—Inferior, triangular in cross section with angles unequally winged, about 9 mm in length and 9 mm in width (excluding wings), color is 145B and becoming 154D at tips of wings.

*Seed*.—Very numerous, ovoid in shape, 172C in color, <0.1 mm in length.

It is claimed:

1. A new and distinct cultivar of *Begonia* plant named 'YABON' as herein illustrated and described.

* * * * *